Figure 1:
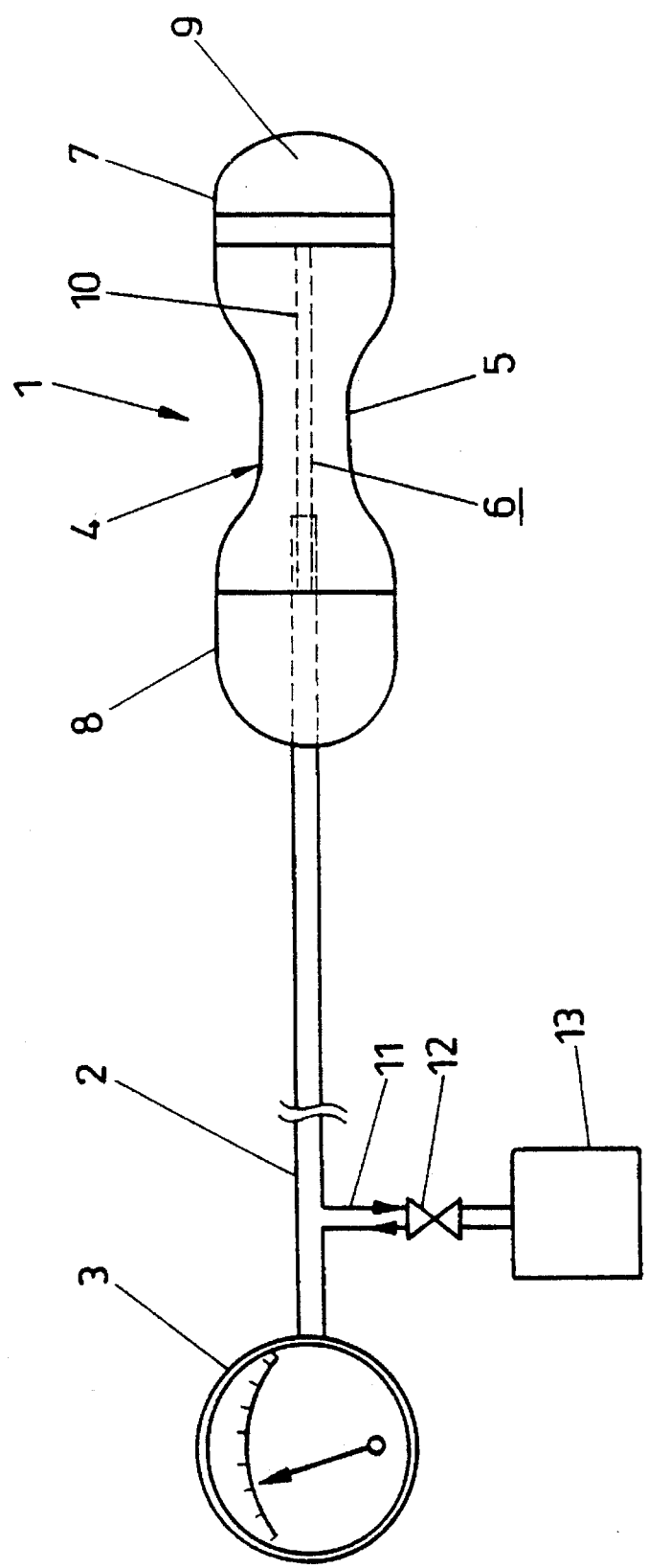

United States Patent [19]
Pauser et al.

[11] Patent Number: 5,483,832
[45] Date of Patent: Jan. 16, 1996

[54] DEVICE FOR MONITORING THE CONTRACTABILITY OF THE PELVIC FLOOR MUSCLES

[76] Inventors: Alexander Pauser, Czartoryskigasse 163, Vienna, Austria, A-1170; Ilse Michl, Dustmannweg 9, Vienna, Austria, A-1160

[21] Appl. No.: 146,095
[22] PCT Filed: Mar. 8, 1993
[86] PCT No.: PCT/AT93/00041
§ 371 Date: Nov. 9, 1993
§ 102(e) Date: Nov. 9, 1993
[87] PCT Pub. No.: WO93/17619
PCT Pub. Date: Nov. 9, 1993

[30] Foreign Application Priority Data

Mar. 9, 1992 [AT] Austria ................ 454/92

[51] Int. Cl.⁶ ................ A61B 5/00; G01L 19/00
[52] U.S. Cl. ................ 73/379.08; 73/379.01; 128/778
[58] Field of Search ................ 128/774, 777, 128/778, 775; 73/379.02, 379.03, 379.08, 379.09

[56] References Cited

U.S. PATENT DOCUMENTS

| | | | |
|---|---|---|---|
| 2,499,045 | 2/1950 | Walker et al. | 128/261 |
| 2,507,858 | 5/1950 | Kegel | 73/379.09 |
| 3,799,170 | 3/1974 | Walsh et al. | 128/344 |
| 4,216,783 | 8/1980 | Kaiser et al. | 73/379.09 |
| 4,566,465 | 1/1986 | Arhan et al. | 128/778 |
| 4,768,522 | 9/1988 | Shapiro | 128/778 |
| 4,873,990 | 10/1989 | Holmes et al. | 128/748 |
| 4,953,563 | 9/1990 | Kaiser et al. | 128/778 |

FOREIGN PATENT DOCUMENTS

| | | |
|---|---|---|
| 2582944 | 12/1986 | France . |
| 157594 | 11/1982 | Germany . |
| 346971 | 6/1960 | Switzerland . |
| 328599 | 4/1930 | United Kingdom . |

Primary Examiner—Hezron E. Williams
Assistant Examiner—R. Biegel
Attorney, Agent, or Firm—Jacobson, Price, Holman & Stern

[57] ABSTRACT

A device for monitoring the contractibility of the pelvic floor muscles is provided in which a probe, having a plurality of elastically deformable chambers, is connected to a fluid filled conduit and a display device, which is connected to the fluid filled conduit. Such a device is effective in obtaining more isolated measurements for muscles being monitored and reducing interference from other muscles. The device can be used therapeutically to monitor progress in training of the pelvic floor muscles.

17 Claims, 5 Drawing Sheets

DEVICE FOR MONITORING THE CONTRACTABILITY OF THE PELVIC FLOOR MUSCLES

The present invention relates to a device for monitoring the contractability of the pelvic floor muscles, wherein a probe is connected by at least one measurement line or conduct to a display.

A device of the type described in the introduction hereto is described, for example, in DD-PS 157 594; in this, a tube that is closed at one end is surrounded by a flexible casing and the effect of the sphincter muscle that is to be monitored on the probe can be seen on an appropriate measuring device. A similar configuration is described in CH-PS 346 971; in this, a cylindrical hollow body can be inflated by means of a compressor that is connected to a manometer. A disadvantage in this configuration is the fact that the stresses that act along the entire length of the probe, will result in an indication without it being possible to say precisely that the indication has been caused by the work done by a specific area of the musculature.

A similar embodiment is described in U.S. Pat. No. 4,768,522; in this, a spring element is imbedded in the probing head in order to permit precise positioning.

DE-OS 32 21 115 describes a device for measuring the contractability of sphincter muscles; in this, a probing head that can be introduced into a bodily orifice has an inner body that is enclosed along part of its length by a hose that is of a thin, elastic, and extensible material. The hose is connected through at least one aperture in the inner body to the interior space of said body. In this known embodiment, the measurement line is configured as a concentric double tube, in which connection it is especially intended that the probe be used, for example, to measure contractions within the intestines, so that the probe must be sufficiently flexible over a wide area.

In the female body, the pelvic floor muscles ensure, amongst other things, the retention of urine and the proper closure of the urethra. The pelvic floor muscles are arranged in a layer and have, essentially, a central sphincter muscle. In women, the pelvic floor muscles are stressed to a relatively high level during pregnancy, which means that the muscles develop a certain amount of strength and force. During birth, however, the pelvic floor muscles are stretched to a very great extent, and even muscles that have been trained to a certain extent during pregnancy cannot immediately resume the desired function after such powerful stretching or over-stretching. As a consequence of this, in particular when a woman has given birth a number of times, the danger of incontinence is particularly great, at least in the period of time after the birth, and for this reason a number of training programs for over-stressed muscles or muscles that cannot completely fulfil their function are offered in hospitals after pregnancy.

In the case of the most frequent indication, namely incontinence, the patient must tighten the pelvic floor muscles, which can be worked at will, by means of specific exercises; when this is done, it must also be ensured that it is, in actual fact, those muscles that are to be trained that are tightened and that other muscles do not simultaneously induce pressure. If known devices are used, the activation of other muscles can give the therapist and the patient a false impression that correct muscle training is taking place, and when exercises of this kind are used it has up to now been impossible to monitor the effects obtained by therapy in any other way.

It is the task of the present invention to create a device of the type described in the introduction hereto, with which a therapeutic program and, in particular, the successes achieved by training, can be monitored and displayed in a simple way. In order to solve this problem, the device according to the present invention is characterized essentially in that the probe has on its periphery at least one pressure sensor or areas that are separated from each other and which can be deformed elastically against a fluid. By having at least one pressure sensor appropriately positioned on the periphery or close to the periphery of the probe, it is possible to monitor the activation of special areas of the musculature. A similar and special monitoring of individual parts of the muscle can also be achieved by an arrangement of a plurality of elastic areas or chambers that are separated from each other and can be deformed by means of a fluid.

In addition to using pressure sensors, for example, in the form of wire strain gauges, as is done in a preferred embodiment, which are then connected by way of an electrical measurement line or conduit to an appropriate measuring device that incorporates an analysis circuit and a display, it is possible to achieve a particularly simple device, above all else, in that there are areas on the probe that can be deformed elastically against a fluid, with the measurement line being preferably in the form of a fluid line or a fluid filled conduit that can be connected with a fluid gauge chamber and a display that is connected to the fluid gauge chamber. In a configuration of this sort, measuring devices that are customarily used in the medical-technical domain, for example for measuring blood pressure, can be used directly, without any substantial modification when, however, it is preferred that a liquid fluid and, in particular, fluids that are generally regarded as harmless be used as the fluid, these being, in particular, aqua bidestillata.

In order to ensure that the device according to the present invention is anchored in a position that is suitable for both measurement and display and does, in point of fact, provide measured values in the area of the musculature that is to be trained, the configuration can advantageously be such that the probe is in the form of an extended body that is constricted in its middle area or chambers, in which connection the middle constricted area of the probe can have an elastically deformable covering, the degree of deformability of this being greater than the deformability of the areas of the probe that are adjacent to the middle area. The contractability of the annular sphincter-like pelvic floor muscles is measured, selectively with an embodiment of this kind, when disruptive effects which would result, by pressure, in particular intestinal pressure, are to a large extent kept away from the point at which the measurements are being made. In order to prevent intestinal pressure of this kind from falsifying the measured values in a roundabout way, i.e. by axial compression, the configuration is advantageously such that the middle area incorporates stiffening that runs in the axial direction of the probe, in particular a rod that is connected to the less-deformable areas (7, 8) that are adjacent to the middle area and passes through the constricted area in an axial direction.

Using the device according to the present invention, it is also possible to display the effect of undesirable intestinal pressure separately, in a particularly simple way. In order to enhance the effects achieved by therapy in this way, such that the patient is made more aware of the musculature that is to be trained, the embodiment can advantageously be so configured that the probe has at its free end at least one separate pressure sensor or a chamber that is defined by an elastically deformable membrane, when a separate measurement line can be connected to a measuring device and display. A second separate pressure sensor of this kind, which is led out by way of a separate line, makes it possible to provide additional measured values that make it readily apparent that any increase in the measured values from this additional pressure sensor cannot further enhance the therapeutic effect that is desired.

In order to increase the training effect and permit adaptability to various starting conditions, the configuration can advantageously be so configured that a source of pressure can be connected to the deformable areas or to the measurement line, with a valve system, in particular a non-return valve, being inserted between them. This makes it possible to pre-set an initial starting pressure in the deformable areas within very wide limits and, as the training of the appropriate musculature progresses, to increase the training effect by increasing the base pressure. In order to ensure simple operation, the measuring device can have a re-settable zero indicator that is independent of the starting pressure that is selected. If a fluid is used as the medium for the pressure display, the source of pressure can be operated with the same fluid and, at the same time, serve as a fluid reservoir. If, for example, pressure sensors in the form of wire strain gauges are used on the periphery of the deformable areas, the source of pressure opens out through a separate line into the deformable areas and can, for example, be configured as a compressed-air source.

If a plurality of separate areas that can be deformed elastically against a fluid are used, according to a preferred embodiment the configuration can be such that there are chambers that are separated from each other in a radial direction, and these can be acted upon with fluid at a different pressure. This makes it possible to oppose the pressure acting from the outside by, for example, a counterpressure that does not increase linearly, whereby the training effect can be improved and increased.

In a preferred embodiment, when the pressure sensor is arranged in the area of the periphery of the probe, the configuration is such that the probe is formed on at least a part of its length from a hollow cylinder that incorporates a gap that extends in the longitudinal direction, and in that at least one wire strain gauge that is connected to the measurement line is arranged on the inside periphery of the cylinder. A configuration of this type is distinguished by a particularly simple production of the hollow cylinder that represents the actual measurement area or sensitive area of the probe, and even very small pressure differentials can be identified by using at least one wire strain gauge so that the smallest deformation of the cylinder will provide a measurement. The cylinder can thus be made relatively stiff, so that the actual shape of the probe remains almost unchanged. When this is done, appropriate matching to anatomical differences can be effected by a differently dimensioned cylinder. In order to optimize measurement results at the smallest pressure loads and thus to manage with relatively simple amplifying and analysis circuits, it is preferred that the configuration is such that the wire strain gauge is arranged opposite the gap.

According to a modified embodiment, in place of using wire strain gauges, the configuration can be such that the probe is formed on at least a part of its length by a hollow cylinder that incorporates a gap that extends in the longitudinal direction; and such that in the area of the gap there are electrically conductive plates that are connected to the measurement line whereby, once again, in the case of very small deformations of the hollow cylinder that forms the sensitive area of the probe, it is possible to arrive at measurement results that can be reproduced with simple means and can be easily evaluated.

In order to increase the compressibility of the sensitive area of the probe, the configuration can advantageously be such that the probe is encased in an elastic material, for example, foam, rubber, or the like.

According to a further preferred embodiment of the present invention, a very simple construction of the probe and in particular of the sensitive area of the probe can be achieved in that the probe incorporates elastic areas in which there is electrically conductive material, for example, carbon dust, electrically conductive liquids or solutions, or the like; and in that electrodes that are connected with the measurement line are embedded in the electrically conductive material. Appropriate selection of the elastic material makes it possible to adjust the compressibility of the device.

In order to provide for easy and simple manipulation and positioning of the probe relative to the parts of the musculature that are to be monitored, the configuration is preferably such that at the end that is opposite to the free end of the probe there is a positioning stop on the probe; in order to achieve exact seating, the configuration is preferably such that the positioning stop is formed from a particularly flexible plastic disk, the outside diameter of this exceeding the diameter of the probe by at least one-third of this diameter.

Manipulation of the device according to the present invention is preferably simplified in a configuration of this sort such that a grip is provided on the positioning stop; in order to provide adaptability to differing anatomical features, the configuration is such that the positioning stop can be secured on the probe at a variable distance from the free end of said probe.

Figure 2:
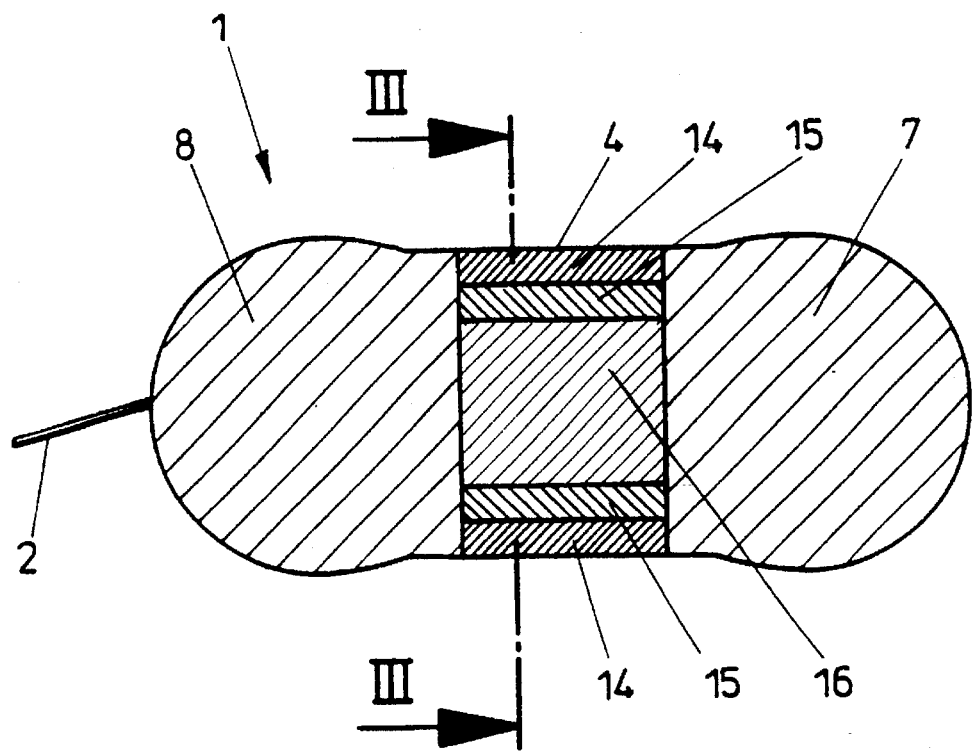
Figure 3:
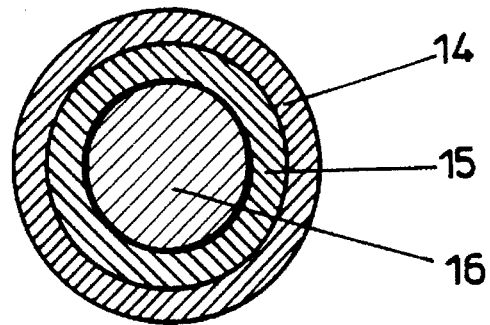
Figure 4:
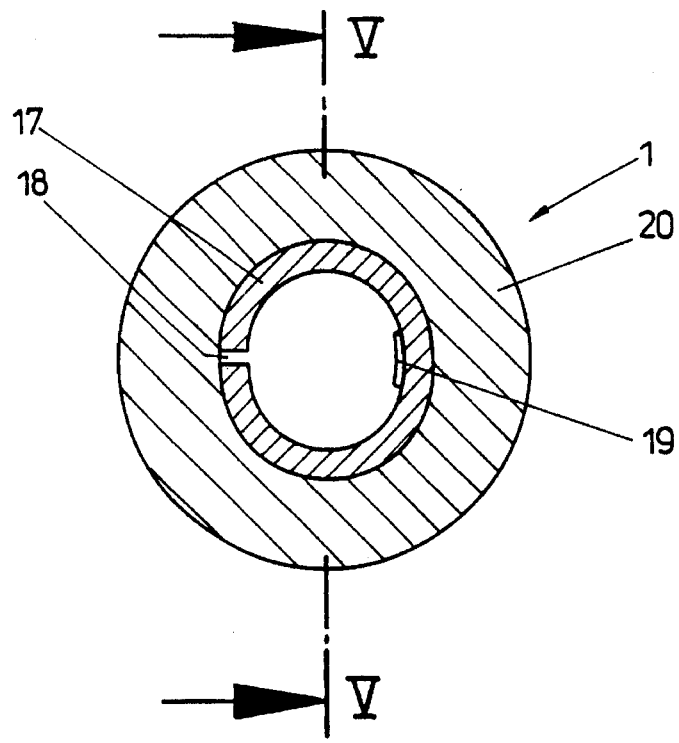
Figure 5:
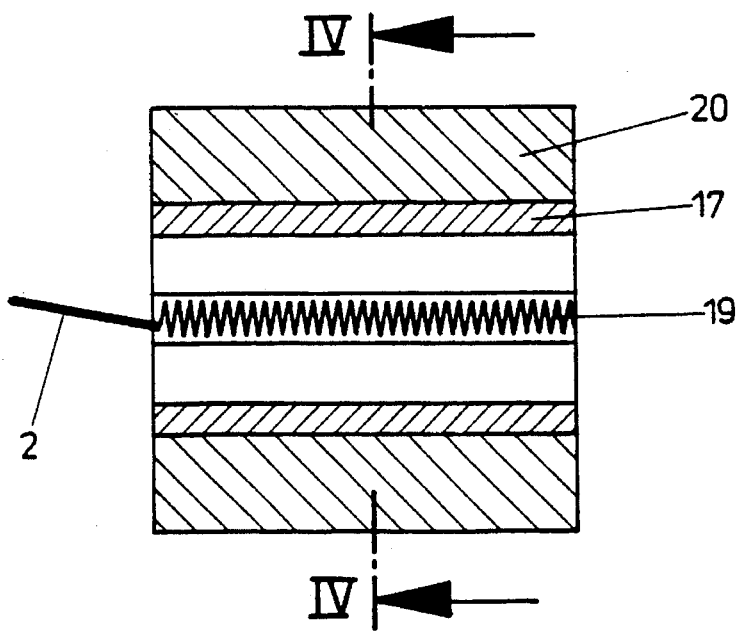
Figure 6:
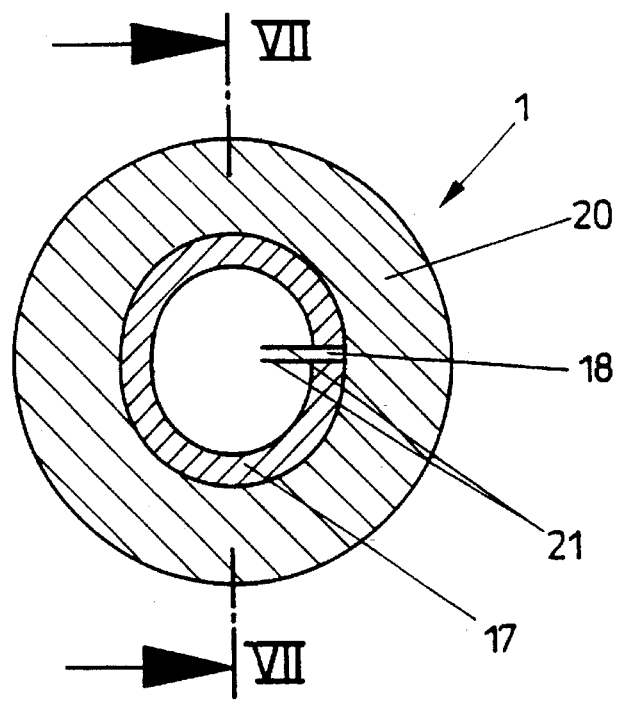
Figure 7:
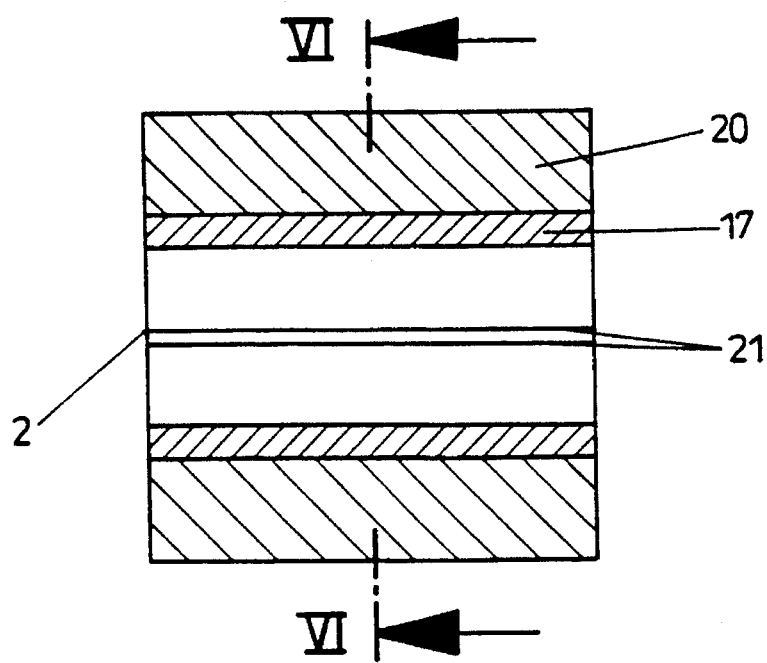
Figure 8:
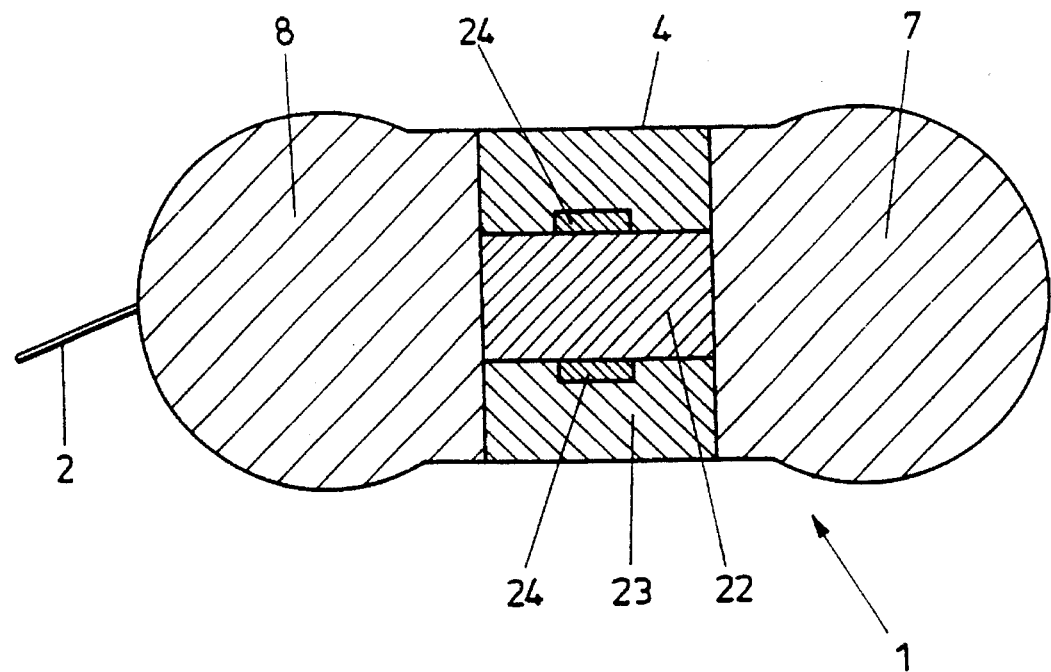
Figure 9:
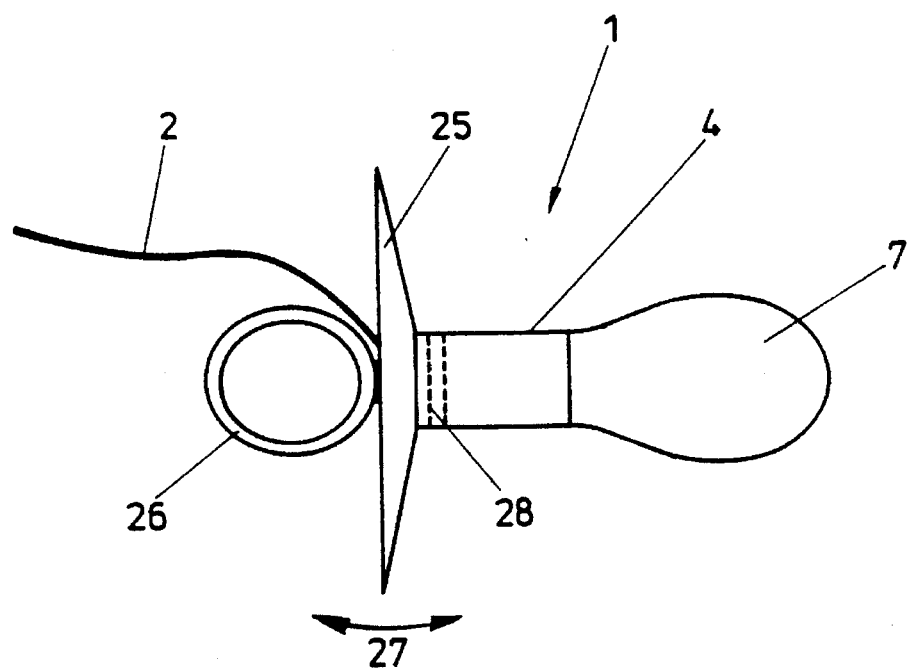

The present invention will be described in greater detail below on the basis of embodiments that are shown in the drawings appended hereto. These drawings show the following:

FIG. 1: a partial cross-section view of a first device according to the present invention;

FIG. 2: a partial cross-section view of a modified embodiment of a probe of a device according to the present invention;

FIG. 3: a cross-section on the line III—III in FIG. 2;

FIG. 4: a cross-section through a modified version of a device according to the present invention, similar to the one shown in FIG. 3, using a wire strain gauge;

FIG. 5: a cross-section on the line V—V in FIG. 4, FIG. 4 being a cross-section on the line IV—IV of FIG. 5;

FIG. 6: a cross-section through a modified version using electrically conductive plates as pressure sensors, similar to FIG. 4;

FIG. 7: a cross-section on the line VII—VII in FIG. 6, FIG. 6 being a cross-section on the line VI—VI of FIG. 7;

FIG. 8: a partial cross-section view through a further modified embodiment of a probe according to the present invention, similar to FIG. 2;

FIG. 9: a schematic view of a further modified probe of a device according to the present invention, with a positioning stop on the probe which can be fixed in different positions.

FIG. 1 shows a probe 1 that is to be introduced into the vagina and which is connected through a measurement line 2 to a measurement and display device 3. At its middle, the probe 1 has a constricted area 4 that is encased by an elastically deformable membrane 5. A fluid line that is connected to a barometric fluid gauge chamber and a display apparatus 3 enters the chamber 6 that is defined by this elastically deformable membrane 5. Comparatively stiffer and less compressible areas 7 and 8 are adjacent to the middle constricted area 4 and, in particular an additional pressure sensor 9 can be arranged in the end area 7 of the probe 1, and this is connected through another fluid or measurement line (not shown herein) to an additional measuring device. Alternatively, the measuring device 2 can have two scales or displays, or can be switchable.

The two comparatively less compressible areas 7, 8 of the probe can be connected to each other through an axial connector or rod 10 in order to prevent compression and thus a rise in pressure in the chamber 6 when pressure is exerted on the end area 8 of the probe.

Furthermore, in order to set a starting pressure at a different level, when the chamber is filled with fluid, a pressure source 13 for the fluid can be connected to the fluid line 2 through a line 11 that incorporates a non-return valve 12. This pressure source 13 also serves as a fluid supply. Alternatively, the line 12 can pass directly into the chamber 6 that is defined by the membrane 5. In order to simplify operation, in this case the measuring device 2 has a re-set button for setting it to a zero position in order to permit monitoring of the training effect, regardless of the starting pressure.

FIGS. 2 and 3 show a modified version in which, in the middle area 4 which represents the measurement area, there is a plurality of chambers 14, 15, 16 that are separated from each other in the radial direction; these are connected through the measurement and fluid line 2 to a measuring device and/or a pressure source, as in the embodiment shown in FIG. 1. The arrangement of a plurality of chambers that are radially separated from each other makes it possible to oppose the pressure acting from outside with a non-linearly increasing counter-pressure, which will increase the training effect. Thus, for example, the pressure in the chamber can increase from the outside inwards so that, essentially, only after compression of the fluid in an outer chamber will the next chamber in an inward direction be acted upon. If a pressure source that is connected to the radial chambers 14, 15, 16 is provided, it is, for example, possible to build up an appropriate non-linear counter-pressure that would correspond to the characteristic curve of a non-linear spring.

In the embodiment shown in FIGS. 4 to 7, the probe 1 is formed to at least part of its axial extent by a hollow cylinder 17; this incorporates a gap 18 that extends in the longitudinal direction. In the embodiment that is shown in FIGS. 4 and 5, a wire strain gauge 19 is arranged on the inside surface of the cylinder, and this is connected once again by a measurement line 2 to an analysis and display device (not shown herein). By using a wire strain gauge, even the smallest effects of pressure on the hollow cylinder can be identified, so that this can be made relatively stiff. In order to provide for optimal signal analysis, the wire strain gauge is arranged opposite the gap 18 in the embodiment that is shown. Because of the known sensitivity of wire strain gauges and in order to increase acceptance of the device, the hollow cylinder 17 is covered in an elastic material 20 when, for example, foam, rubber, or the like can be used for this material.

The embodiment that is shown in FIGS. 6 and 7 differs from the preceding embodiments in that within the area of the gap 18, there are electrically conductive plates 21 which together form a condenser. By deformation of the cylinder when the pressure loads are working on it, the electrically conductive plates 21 that form a condenser can provide a measurement value which permits direct monitoring of the contractability of the pelvic floor muscles.

In the configuration shown in FIG. 8, an elastic, sponge-like, electrically non-conductive material 23 is incorporated about a cylindrical core 22. A material is incorporated in the pores of the material 23; this has a specific electrical conductivity and can be in the form of carbon dust, electrically conducted liquids or solutions, or the like. Electrodes 24 are embedded in the material 23 and these are once again connected to the measurement line 2. Compression of the material 23 presses the pores together, which means that the contact surface for the electrically conductive material is changed, and this can once again provide an appropriate signal.

In the configuration shown in FIG. 9, the measurement area 4 of the probe 1 can be configured as in one of the preceding embodiments. In order to provide for improved manipulation and simpler application, as well as to maintain the same position in each instance, in this embodiment there is a positioning stop 25 that can be formed, for example, from a flexible plastic plate. The outside diameter of the positioning stop 25 is greater than the diameter of the probe 1. In order to provide a grip on the probe 1, there is a grip 26 on the stop 25 that is formed from a plastic plate. In order to match the positioning, the positioning stop 25 can be moved and secured in different positions relative to the measurement area 4 of the probe, as is indicated by the double-headed arrow 27. This can be secured very simply by being snapped into different positions; there are grooves 28 in which corresponding projections on the stop 25 can snap into position.

In addition, bi-metal pressure sensors can also be used.

We claim:

1. A device for monitoring the contractibility of the pelvic floor muscles comprising a probe having a first end and a second end, a plurality of chambers, each defined by an elastically deformable membrane, at least one of the plurality of chambers being fluid filled; at least one of the plurality of chambers being positioned intermediate the first and second ends and having a constricted region;

at least one fluid filled conduit having two ends, one of the ends being connected to the at least one fluid filled chamber by way of fluid communication with the fluid filled chamber; and a display device, connected to and in communication with, the other end of the fluid filled conduit.

2. The device of claim 1 wherein at least one of the plurality of chambers is positioned at the first end of the probe and is adjacent the intermediate chamber; at least one of the plurality of chambers is positioned at the second end of the probe and is adjacent the intermediate chamber; and the elastic deformability of the membrane defining the intermediate chamber is greater than the elastic deformability of the membrane defining the chambers positioned at each of the first and second ends of the probe.

3. The device of claim 1 wherein the at least one fluid filled conduit is connected to and in communication with, a fluid gauge chamber and wherein the display device, which is connected to the fluid filled conduit, is connected to and in communication with, the fluid gauge chamber.

4. The device of claim 1 wherein the intermediate chamber comprises a stiffening means, extending in a direction commensurate with the length of the probe.

5. The device of claim 4 further comprising at least one of the plurality of chambers positioned at the first end of the probe adjacent to the intermediate chamber and at least one of the plurality of chamber positioned at the second end of the probe adjacent the intermediate chamber and wherein the stiffening means is a rod which extends from the first end chamber to the second end chamber, through the constricted region of the intermediate chamber.

6. The device of claim 1 wherein at least one of the plurality of chambers is located at the first end of the probe and comprises a pressure sensor and a second conduit for measuring pressure exerted by means other than the muscles being monitored.

7. The device of claim 6 wherein the second conduit is fluid filled and is connected to and in communication with, a display device and a measurement device.

8. The device as defined in claim 1 further comprising a pressure source connected, by way of fluid communication, to the at least one fluid filled chamber, for applying pressure to the at least one fluid filled chamber.

9. The device as defined in claim 1 wherein the fluid is aqua bidestillata.

10. The device as defined in claim 1 wherein the plurality of chambers are radially separated and wherein each chamber may be pressurized by a fluid at different pressures.

11. The device as defined in claim 1 further comprising a pressure source, connected by way of fluid communication, to the fluid filled conduit, for applying pressure to the at least one fluid filled chamber, which is in fluid communication with the fluid filled conduit, wherein a valve is positioned between the pressure source and the fluid filled conduit for limiting the application of pressure in one direction.

12. The device of claim 1 wherein the probe is substantially cylindrical and has a positioning stop arranged on the second end of the probe.

13. The device of claim 12 wherein the positioning stop is capable of being positioned at varying distances from the second end of the probe.

14. The device of claim 12 wherein the positioning stop comprises a flexible plastic plate having a diameter which exceeds the largest diameter of the probe by at least one third.

15. The device of claim 12 wherein the positioning stop further comprises a grip.

16. A device for monitoring the contractibility of the pelvic floor muscles comprising a probe having a first end and a second end, a plurality of chambers, each defined by an elastically deformable membrane, at least one of the plurality of chambers being fluid filled; at least one of the plurality of chambers being positioned intermediate the first and second ends;

at least one fluid filled conduit having two ends, one of the ends being connected to the at least one fluid filled chamber by way of fluid communication with the fluid filled chamber;

a display device, connected to an in communication with, the fluid filled conduit;

at least one of the plurality of chambers located at the first end of the probe and having a pressure sensor and a second conduit for measuring pressure exerted by means other than the contractibility of the muscle being monitored.

17. A device for monitoring the contractibility of the pelvic floor muscles comprising a probe having a first end and a second end, a plurality of chambers, each defined by an elastically deformable membrane, at least one of the plurality of chambers being fluid filled; at least one of the plurality of chambers being positioned intermediate the first and second ends;

at least one fluid filled conduit having two ends, one of the ends being connected to the at least one fluid filled chamber by way of fluid communication with the fluid filled chamber;

a display device, connected to and in communication with, the other end of the fluid filled conduit; and wherein the plurality of chambers are radially separated and wherein each chamber is pressured by a fluid at different pressures.

* * * * *